United States Patent [19]

Renfrew et al.

[11] Patent Number: 6,007,689
[45] Date of Patent: *Dec. 28, 1999

[54] APPARATUS FOR PREPARING GELS FOR USE IN ELECTROPHORETIC SEPARATIONS AND SIMILAR APPLICATIONS

[75] Inventors: John A. Renfrew, Burlington; Eric Steinbach; John K. Stevens, both of Toronto; Henryk Zaleski, Niagara Falls, all of Canada

[73] Assignee: Visible Genetics Inc., Toronto, Canada

[ * ] Notice: This patent is subject to a terminal disclaimer.

[21] Appl. No.: 08/836,268

[22] PCT Filed: Oct. 31, 1995

[86] PCT No.: PCT/US95/13955

§ 371 Date: May 1, 1997

§ 102(e) Date: May 1, 1997

[87] PCT Pub. No.: WO96/13715

PCT Pub. Date: May 9, 1996

Related U.S. Application Data

[63] Continuation-in-part of application No. 08/332,892, Nov. 1, 1994, Pat. No. 5,507,934.

[51] Int. Cl.$^6$ .................................................. G01N 27/26
[52] U.S. Cl. .................. 204/470; 204/620; 204/457; 204/608; 425/174
[58] Field of Search ................................... 204/456, 457, 204/465–467, 469, 470, 606, 607, 615–620; 604/87, 88; 264/425, 463, 494, 496; 425/174

[56] References Cited

U.S. PATENT DOCUMENTS

| | | |
|---|---|---|
| 3,756,390 | 9/1973 | Abbey et al. . |
| 3,867,271 | 2/1975 | Hoefer ............................. 204/180 G |
| 4,416,761 | 11/1983 | Brown et al. ...................... 204/299 R |
| 4,652,354 | 3/1987 | Place et al. ........................... 204/470 |
| 4,693,706 | 9/1987 | Ennis, III .............................. 604/87 |
| 4,704,198 | 11/1987 | Ebersole et al. ................... 204/182.8 |
| 4,715,943 | 12/1987 | Place et al. ........................ 204/299 R |
| 4,790,919 | 12/1988 | Baylor, Jr. ......................... 204/182.8 |
| 4,811,218 | 3/1989 | Hunkapiller ...................... 364/413.01 |
| 4,823,007 | 4/1989 | Hanson ............................. 250/327.2 |
| 4,834,854 | 5/1989 | Sugihara et al. .................. 204/182.8 |
| 4,840,756 | 6/1989 | Ebersole et al. ....................... 264/22 |
| 4,844,786 | 7/1989 | Sugihara et al. .................. 204/299 R |

(List continued on next page.)

FOREIGN PATENT DOCUMENTS

| | | |
|---|---|---|
| 0304195 | 2/1989 | European Pat. Off. . |
| 0492769 | 7/1992 | European Pat. Off. . |
| 0555143 | 8/1993 | European Pat. Off. . |
| 0607495 | 7/1994 | European Pat. Off. . |

OTHER PUBLICATIONS

Current Protocols in Molecular Biology, Section 10.2.1–10.2.21, John Wiley & Sons (1991).

*Primary Examiner*—William H. Beisner
*Attorney, Agent, or Firm*—Oppedahl & Larson

[57] ABSTRACT

An apparatus for the rapid preparation of electrophoresis gels comprises: (a) a housing; (b) a support fixture removably disposed within the housing and adapted to receive a gel holder having an internal gel compartment, the support fixture being optionally adapted to permit filling of the gel holder within the housing; (c) an optional injection system, which is connectible to a reservoir for holding a polymerizable solution; (d) an optional solution injection connector adapted to couple the injection system to a gel holder placed within the filling fixture, (e) an optional controller for the injection system, which causes the injection system to inject polymerizable solution from the reservoir into the gel compartment; and (f) a radiation source disposed within the housing in a location effective to irradiate polymierizable solution within the gel compartment of a gel holder in the support fixture. The support fixture may be mounted on a drawer which is slidable between a position inside the housing, and a position outside the housing to permit easy placement of a gel holder into the support fixture.

20 Claims, 6 Drawing Sheets

U.S. PATENT DOCUMENTS

| | | | |
|---|---|---|---|
| 4,863,647 | 9/1989 | Baylor, Jr. | 264/22 |
| 4,929,329 | 5/1990 | Danby et al. | 204/299 R |
| 4,971,677 | 11/1990 | Kambara et al. | 204/299 R |
| 4,985,128 | 1/1991 | Ebersole et al. | 204/182.8 |
| 4,999,340 | 3/1991 | Hoffman et al. | 514/23 |
| 5,047,135 | 9/1991 | Nieman | 204/299 R |
| 5,051,162 | 9/1991 | Kambara et al. | 204/299 R |
| 5,062,942 | 11/1991 | Kambara et al. | 204/299 R |
| 5,069,769 | 12/1991 | Fujimiya et al. | 204/182.91 |
| 5,069,773 | 12/1991 | Frangioni | 204/299 R |
| 5,071,531 | 12/1991 | Soane | 204/182.8 |
| 5,091,652 | 2/1992 | Mathies et al. | 250/458.1 |
| 5,092,973 | 3/1992 | Zare et al. | 204/182.1 |
| 5,119,316 | 6/1992 | Dam et al. | 364/498 |
| 5,122,345 | 6/1992 | Tabor et al. | 422/116 |
| 5,164,066 | 11/1992 | Yetman et al. | 204/299 R |
| 5,186,807 | 2/1993 | Sanford et al. | 204/299 R |
| 5,192,412 | 3/1993 | Kambara et al. | 204/299 R |
| 5,209,831 | 5/1993 | MacConnell | 204/299 R |
| 5,228,971 | 7/1993 | Brumley, Jr. et al. | 204/299 R |
| 5,306,404 | 4/1994 | Notsu | 204/182.8 |
| 5,338,426 | 8/1994 | Shigeura et al. | 204/299 R |
| 5,364,350 | 11/1994 | Dittmann . | |
| 5,365,455 | 11/1994 | Tibbetts et al. | 364/497 |
| 5,507,934 | 4/1996 | Renfrew . | |
| 5,543,097 | 8/1996 | Fang | 204/470 |
| 5,627,022 | 5/1997 | Renfrew et al. . | |

APPARATUS FOR PREPARING GELS FOR USE IN ELECTROPHORETIC SEPARATIONS AND SIMILAR APPLICATIONS

This application is a continuation-in-part of U.S. patent application Ser. No. 332,892 filed Nov. 1, 1994, now U.S. Pat. No. 5,507,934.

I. BACKGROUND OF THE INVENTION

This application relates to an apparatus for preparing gels particularly polyaciylamide gels, for use in electrophoretic separation of biomolecules and similar applications.

Polyacrylamide gel electrophoresis (PAGE) separation of biomolecules is now routinely performed. *Current Protocols in Molecular Biology,* Chap. 10, John Wiley & Sons, (1994). A polyacrylamide gel provides a suitably insoluble sieve that separates biomolecules in solution by size and conformation as they are drawn through the sieve under electromotive force. Such separation of biomolecules provides valuable insights into their structures and functions. For example, PAGE separation can separate two polypeptides of the same size but of different isoforms or polypeptides only 100 daltons difference in size (Current Protocols, 1994). Another use for PAGE is in separation of nucleic acids based on size of fragments, such as in the extremely important application of DNA sequence determination. Maniatis et al., *Molecular Cloning: A Laboratory Manual,* 2nd ed., Chap. 13 (1987).

The prior art on PAGE is extensive. Many patents and scientific papers disclose uses for PAGE in research applications. DNA sequencing may be carried out using automated systems designed for laboratory application. These techniques have historically been important for sequencing long stretches of unknown DNA, such as is the focus of the Human Genome Project. Methods and apparatus for sequencing of DNA are described in U.S. Pat. Nos. 4,811,218; 4,823,007; 5,062,942; 5,091,652; 5,119,316; 5,122,345; 5,228,971, and 5,338,426 which are incorporated herein by reference.

Unfortunately, the traditional techniques for preparation of gels for use in electrophoresis are inadequate for use in clinical diagnostic services, such as the emerging field of clinical diagnostic DNA sequencing. For clinical diagnostic DNA sequencing purposes, it is desirable to sequence hundreds of DNA sequences per day. Existing methods do not provide for such capacity. For example, typical methods of DNA sequencing require that a skilled technician spend up to four hours constructing a gel holder, filling the gel holder with actively polymerizing acrylamide solution, inserting a well-forming comb before substantial polymerization has occurred, and then waiting for the gel to polymerize. (U.S. Pat. Nos. 5,338,426; 5,069,773; Maniatis, 1987). Using the gel is equally cumbersome. Loading sample to be electrophoresed requires painstaking care to ensure the integrity of loading wells and to prevent samples from running together. Thus, in order to make maximum clinical use of the opportunities presented by our ever increasing, knowledge of the human genetics and the genetic causes of many disease, it would be advantageous to have a method of rapidly making polyacrylamide gels which are convenient for more efficient sample loading and running, particularly for use in clinical diagnostic applications.

It is an object of the invention to provide an apparatus for filling a gel holder with a polymerizable solution, and catalyzing the polymerization of the solution using ultraviolet light to form a gel usable for electrophoretic separation of biomolecules, particularly nucleic acids.

It is a further object of the invention to provide a cartridge for use as a reservoir in the gel filling and polymerizing apparatus of the invention.

It is a further object of the invention to provide an apparatus for polymerizing an already filled gel holder.

It is a further object of the invention to provide a method for preparing an electrophoresis gel which uses the apparatus of the invention.

It is a further object of the invention to provide an apparatus for the rapid and convenient formation of gels which are more easily loaded with sample.

II. SUMMARY OF THE INVENTION

These and other objects are achieved using an apparatus specifically designed for the rapid filling and polymerization of electrophoresis gels. This apparatus comprises:

(a) a housing;

(b) a filling fixture removably disposed within the housing and adapted to receive a gel holder having an internal gel compartment;

(c) an injection systems which is connectible to a reservoir for holding a polymerizable solution;

(d) a solution injection connector adapted to couple the injection system to a gel holder placed within the filling fixture, (e) a controller for the injection system, which causes the injection system to inject polymerizable solution from the reservoir into the gel compartment; and (f) a radiation source disposed within the housing in a location effective to irradiate polymerizable solution within the gel compartment of a gel holder in the filling fixture. In a preferred embodiment of the apparatus, the filling fixture is mounted on a base which is slidable between a position inside the housing and a position outside the housing to permit easy placement of a gel holder into the filling fixture.

III. BRIEF DESCRIPTION OF THE DRAWINGS

Figure 3A:
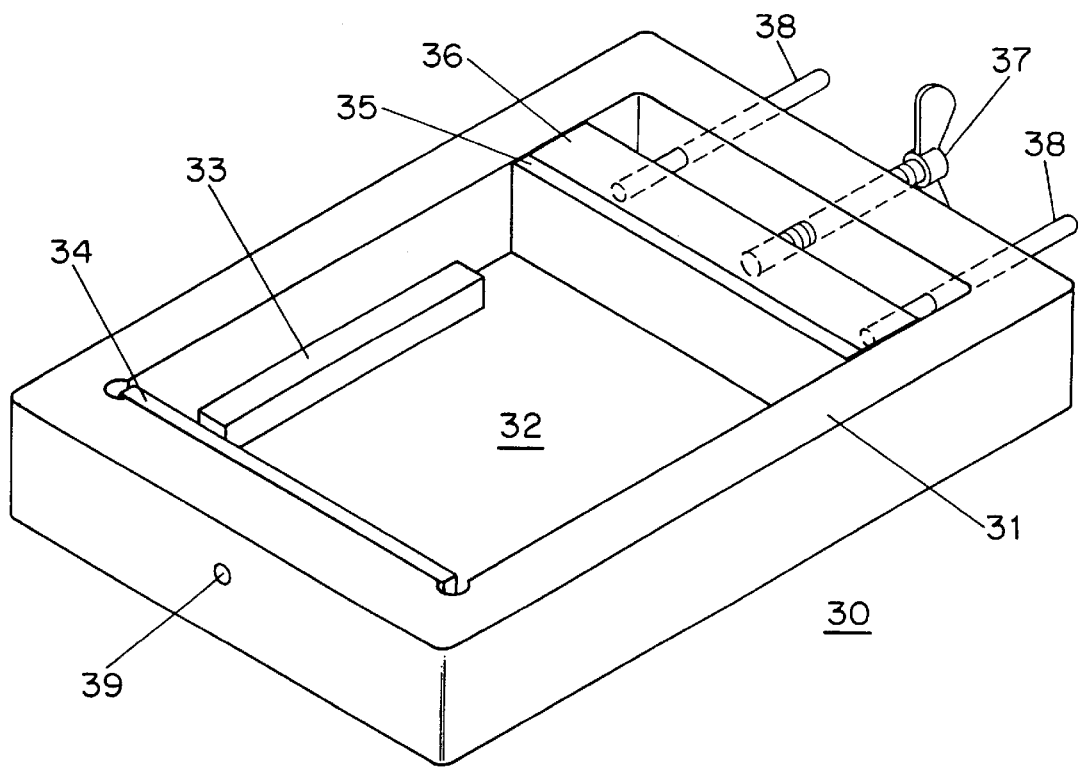
Figure 4:
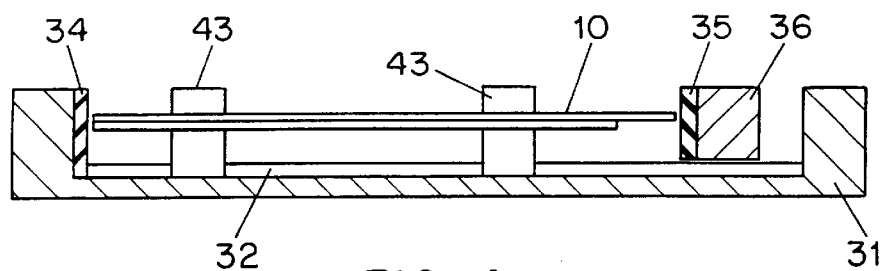
Figure 5:
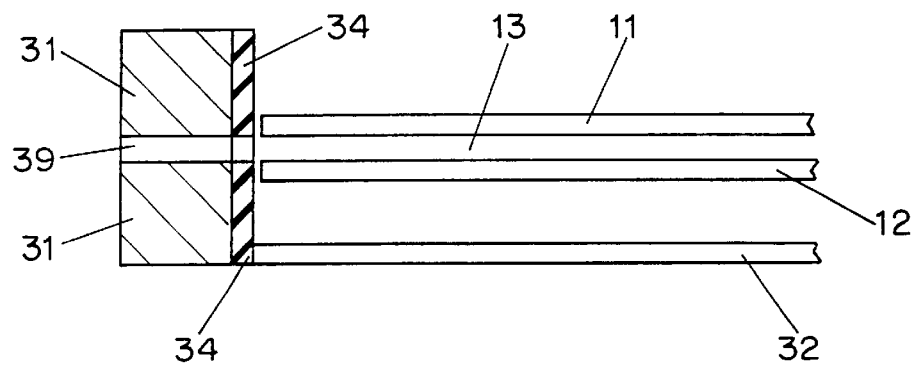
Figure 6:
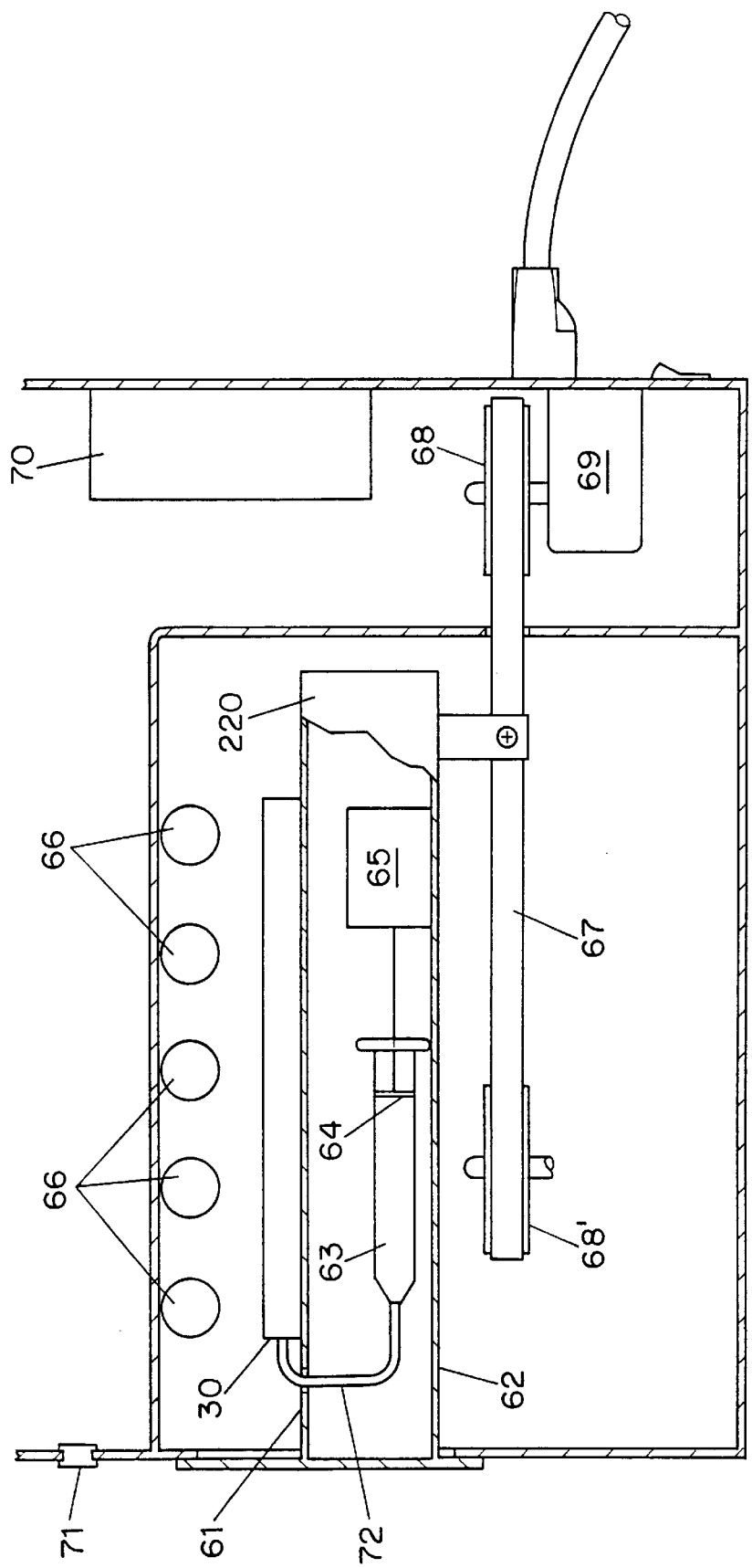
Figure 7:
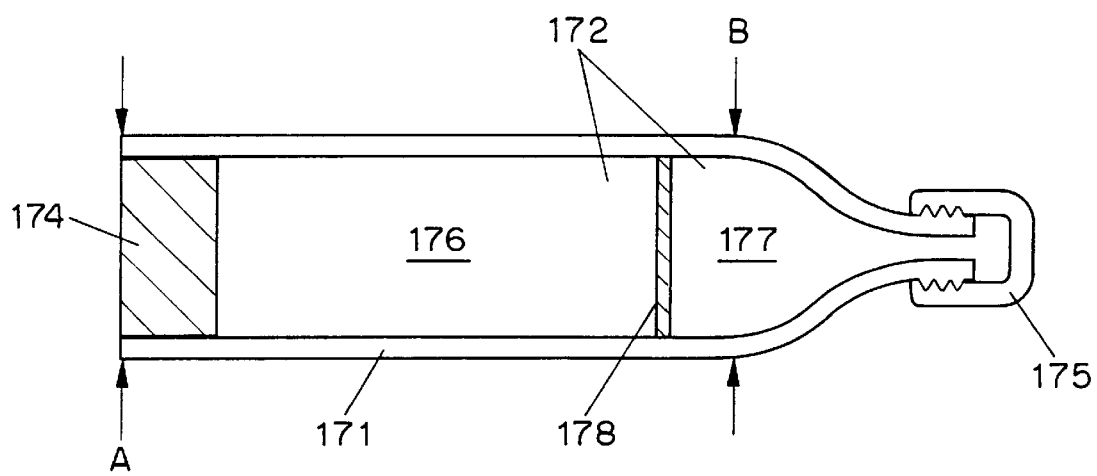
Figure 8:
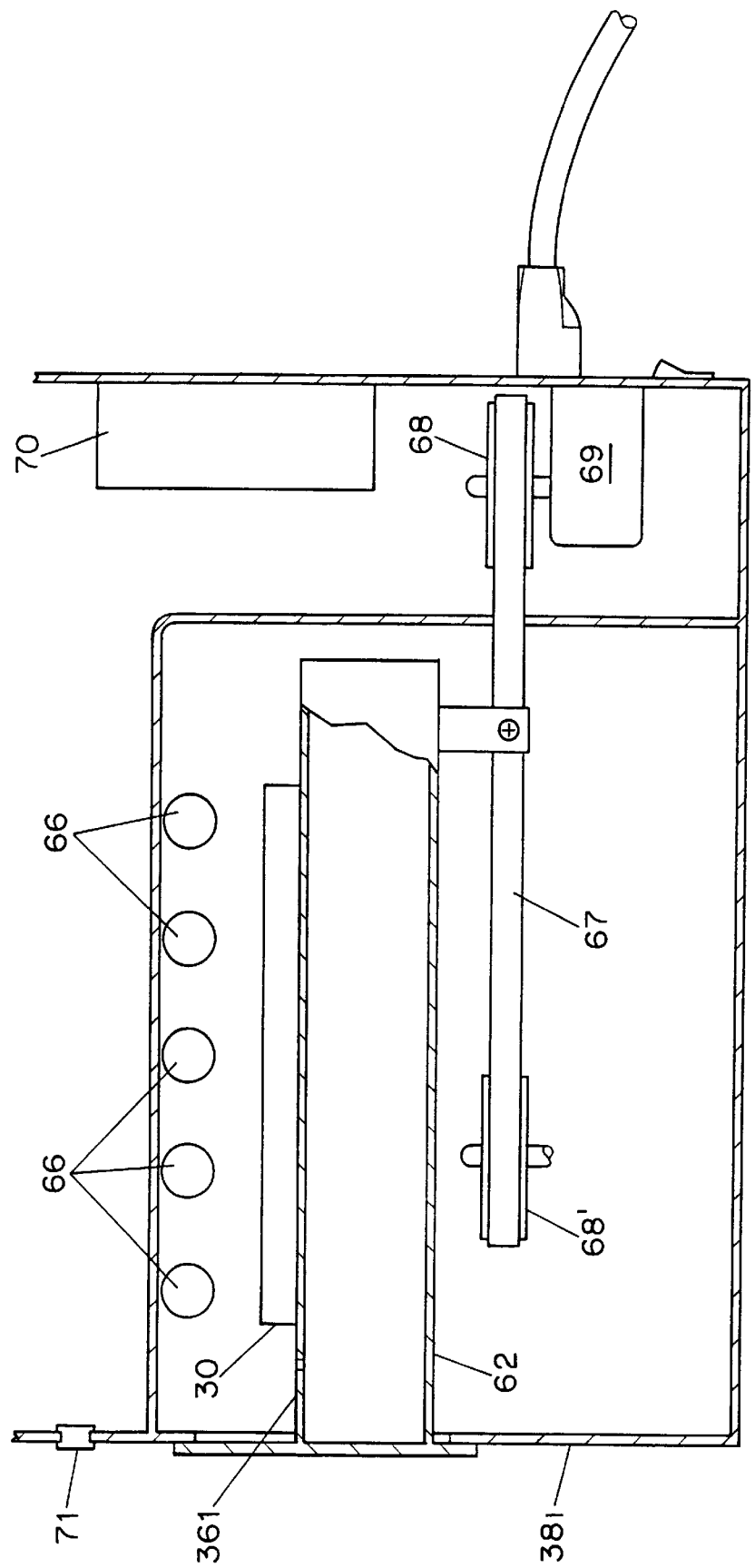

FIGS. 3A and B shows a filling fixture for use in accordance with the invention;

FIG. 4 shows a side sectional view of a filling fixture for use in accordance with the invention having a gel holder positioned therein;

FIG. 5 shows a detailed view of the connection between the injection system and the gel holder;

FIG. 6 shows a cross-sectional view of an embodiment of the invention;

FIG. 7 is a cross-section through a disposable cartridge useful as a reservoir for polymerizable solution;

FIG. 8 shows a gel polymerization apparatus according to the invention; and

Figure 9:
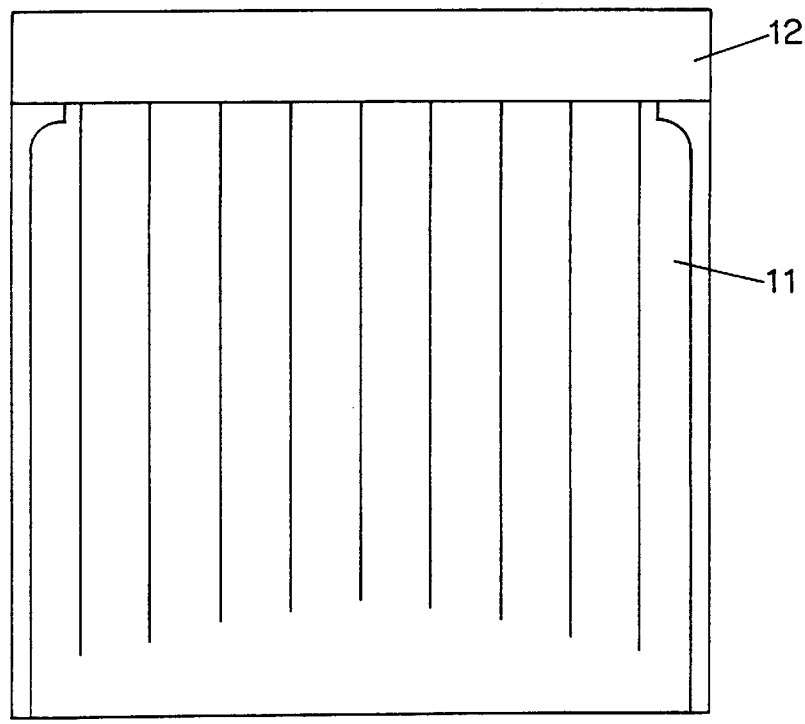

FIG. 9 shows a top view of a gel holder for use in accordance with the invention.

IV. DETAILED DESCRIPTION OF THE INVENTION

Figure 1:
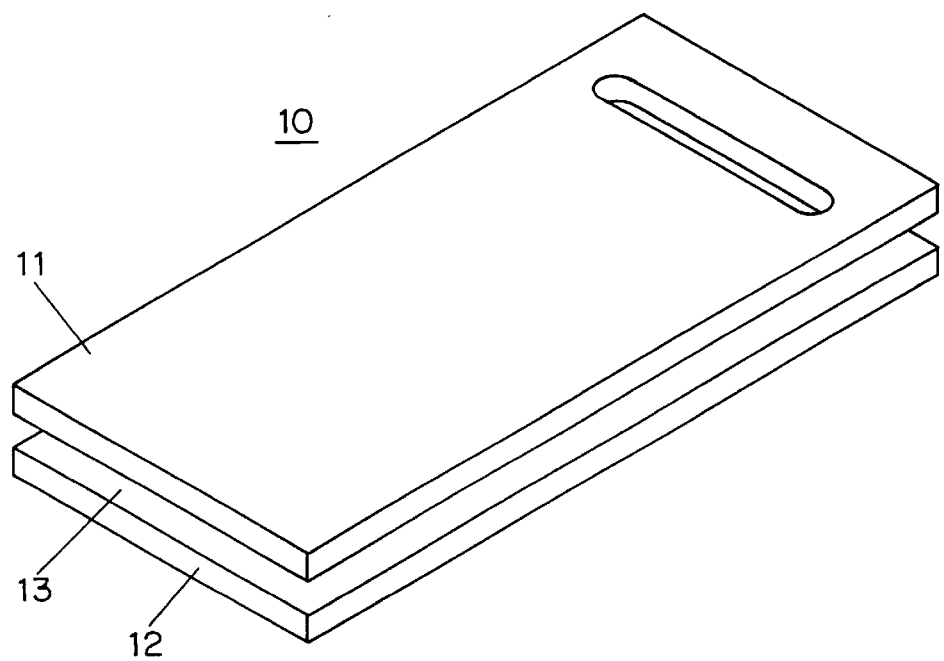
FIG. 1 shows a gel holder which may be filled and polymerized using the method and apparatus of the invention.

The present invention provides an apparatus for the filling of a pre-formed gel holder, and for the polymerization of the gel within the holder. Preferred gel holders are those described in commonly assigned U.S. patent application Ser. No. 08/332,557 and the PCT Application No. PCT/US95/14531 (WO96/13717)being concurrently filed herewith which is a continuation-in-part of said U.S. application, which applications are incorporated herein by reference. As shown in FIG. 1, such gel-holders 10 generally comprise a top substrate 11, a bottom substrate 12, and means 13 for scaling the top substrate 11 to the bottom substrate 12 to form a gel compartment having a thickness of 250 microns or less. The means 13 for sealing has an opening therethrough for filling the gel compartment with an unpolymerized gel. The means for sealing may take the form of an adhesive applied between the top and bottom substrates along at least two opposing edges of the top and bottom substrates.

The separation between the two substrates, and thus the size of the gel compartment is advantageously defined and maintained using a spacer. One form which the spacer may take is a plurality of solid particles disposed between the top and bottom substrate and having a mean diameter substantially equal to the thickness of the gel compartment. Advantageously, at least a portion of these particles are disposed within the adhesive.

Suitable adhesives for use in such gel holders are acrylate adhesives. In some cases, however, there may be an interference between materials in the adhesive and the subsequent polymerization of the gel. For this reason, it may be preferable to affix the solid particles to the top or bottom substrate by forming a mixture of a powder of a low melting glass with a plurality of the solid particles; dispersing the mixture on a surface of the substrate for example by screen printing; heating the substrate and mixture to melt the low melting glass powder; and cooling the heated substrate to resolidify the low melting glass, whereby a bond between the solid particles and the substrate is formed.

Figure 2:
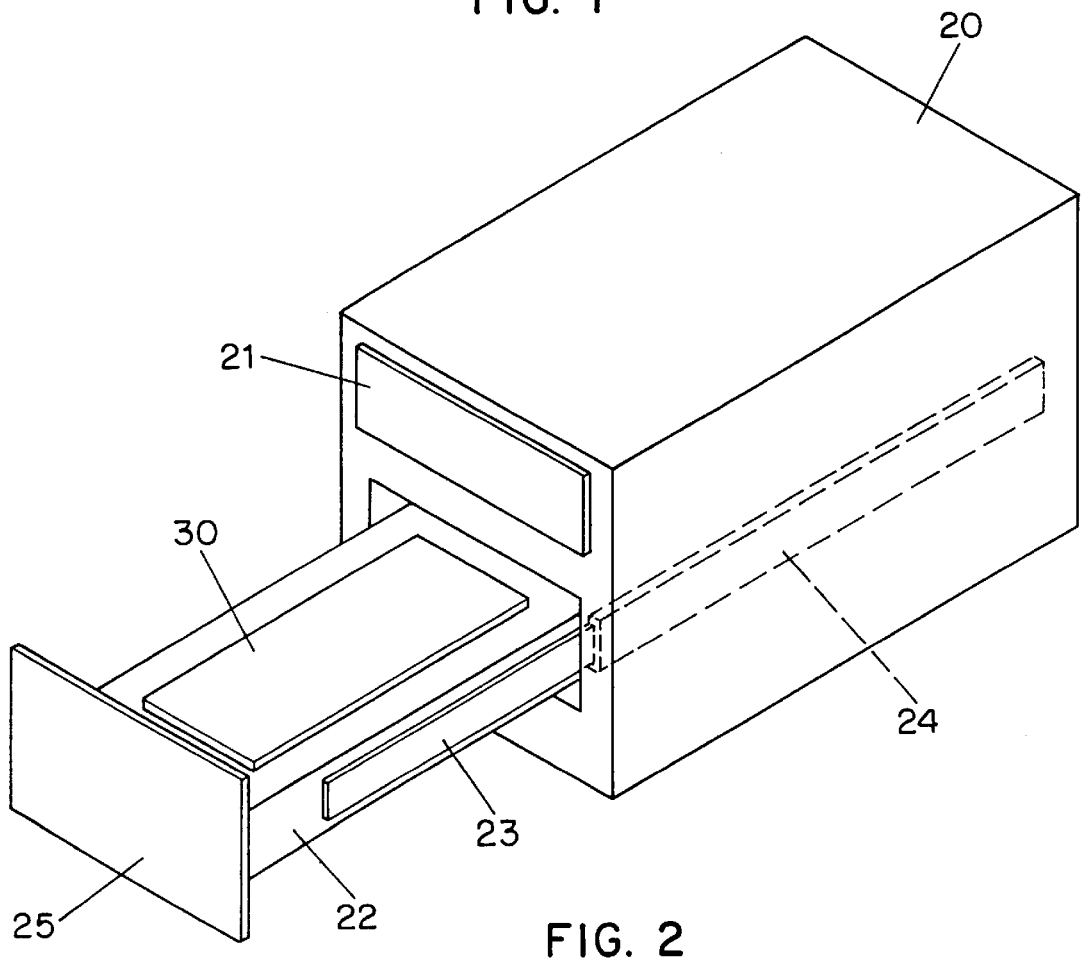
FIG. 2 shows an exterior view of an apparatus according to the invention.

FIG. 2 shows an exterior view of an apparatus in accordance with the invention. As indicated, the apparatus is disposed within a housing 20. Inside the housing is a radiation source such as an ultraviolet lamp or bank of lamps for use in initiating polymerization of the gel. Preferably, the radiation source is positioned so that the total radiation received by any one part of the gel holder is the same as any other. If a number of identical lamps are used, this may require that the lamps be spaced more closely together at the edges than at the center of the gel.

A control panel 21 and a sliding drawer unit 22 are positioned on a front face of the housing 20. Tracks 23 are attached at on sides of the drawer unit 22. The tracks 23 fit into sliding track guides 24 (shown in phantom in FIG. 2) mounted on each side inside the housing 20. At its full extension, the sliding tracks 23 are retained in the sliding track guides 24 by track stops (not shown). At its full retraction the sliding of the drawer is stopped by contact of the face 25 of the drawer with the housing 20. Any sliding means with low coefficient of friction may be employed to bear the weight of the drawer, such as ball bearings, Teflon, wheels or rubber.

Figure 3B:
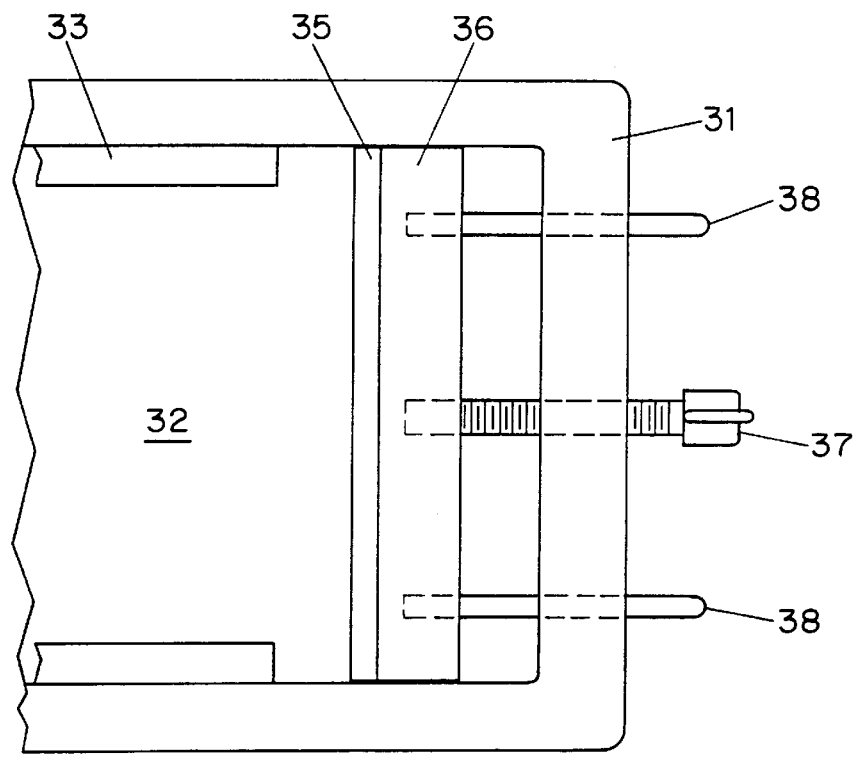

The drawer unit 22 supports a filling fixture 30 such as that shown in FIGS. 3A, 3B and 4. The filling fixture 30 has a rectangular frame 31 surrounding a central base region 32 sized to receive a gel holder. The gel holder rests over the central base region 32 and is supported underneath along each side by a narrow (~3 mm) ledge 33 protruding from the filling fixture. Alternatively, the gel holder 10 may be supported by and held between support members 43 running across the central base region 32 as shown in FIG. 4.

When first placed in the filling fixture, the open end of the microgel holder loosely contacts a silicon strip 34 at the bottom of the filling fixture 30. At the top of the filling fixture, a silicon strip 35 attached to an adjustable bar 36 running widthwise at the top of the filling fixture 30 loosely contacts the top end of the gel holder. By means of a screw 37 or other force directing means, such as a lever, the silicon strip 35 on the moveable bar 36 is placed in close contact with the top of the gel holder and the bottom of the gel holder is thereby secured in close, sealing contact with the silicon strips 34 and 35 at the bottom and top of the filling fixture 30. Fixed guide bolts 38 which slide within openings in the frame 31 ensure that the moveable bar 36 is stabilized and directed smoothly in the direction of the force of the screw 37.

The bottom end of the filling fixture 30 and the silicon strip 34 have an injection port 39 passing through them. When the gel holder is properly secured in the filling fixture 30, the injection port 39 is aligned with the open bottom edge of the gel holder 10 as shown in FIG. 5, providing a pathway for injection of a polymerizable solution into the gel compartment 13 of the gel holder 10. Thus, the silicon strip 34 serves as a solution injection connector and is adapted to couple the injection system to a gel holder placed within the filling fixture.

When the microgel holder is secured in the filling fixture it is ready to be filled and polymerized. Filling and polymerization takes place inside the housing 20. The drawer unit 22 containing gel holder 10, in the filling fixture 30, is slid inwards into the housing 20. In a preferred embodiment of the invention, closing the drawer starts an automated filling and curing process in which polymerizable solution is pumped into the gel holder, and an ultraviolet light disposed within the housing 20 over the gel holder is activated to initiate the polymerization reaction.

FIG. 6 shows a cross-sectional view of one embodiment of the invention in which a two level drawer unit 220 is utilized. As shown, the filling fixture 30 with the gel holder disposed therein is disposed on the upper shelf 61 of the drawer unit 220. A lower shelf 62 supports the solution injection system which is connected to the solution injection port of the top shelf by a tube 72.

The solution injection system comprises a canister 63 of gel forming solution. The solution employed may be an acrylamide solution, with or without urea or sodium dodecyl sulphate (SDS), and with or without any other chemical additives, alternatively it may be any non-acrylamide monomer which exists in solution at or around room temperature and can be polymerized in the presence of ultraviolet light, either with or without further additives.

The canister 63 contains a plunger 64 operatively connected to a motor 65. When the motor is activated, the plunger 64 is driven by the dedicated motor 65 for a predetermined period of time to dispense the correct amount of gel forming solution into the gel holder. In addition, fan 70 may be turned on at the motor to provide venting and heat dissipation inside the housing as part of the process of starting the filling and polymerization cycle, or it may be activated separately.

The injected solution flows evenly through the gel compartment, filling the compartment. Air escapes from the gel compartment through the openings in the window of the top substrate. After the gel compartment has been filled, UV lamps 66 disposed in the top of the housing are activated for a period of time sufficient to polymerize the gel in the holder. For example, using five 20 Watt UVA lamps an acrylamide solution in a gel holder will be fully polymerized in about 5 to 10 minutes. The apparatus then shuts off the lamps and signals completion of the cycle, for example by opening the drawer unit, by sounding an audible alarm or by lighting a signal light.

Activation of the motor 65 to start the gel filling and polymerization cycle can be accomplished by any of several means. First, the cycle can be initiated in response to a command or series of commands entered through the control panel 21 on the front of the housing 20, or the activation of a "start" switch. In the simplest embodiment of the invention, each phase of the processing is started separately by an operator. Thus, a command is entered to start the filling process, and then a second command is entered after the filling process is complete to energize the lamps inside the housing and begin the polymerization part of the cycle.

Preferably, the apparatus will include a mechanism for the controlling the performance of a complete filling and polymerization cycle in response to a single initiation signal. Thus, for example, the apparatus may include a user interface circuit board ("UI Circuit Board") which automatically coordinates the filling/polymerization cycle. The UI Circuit Board is connected to a microprocessor which controls the motor 65 for gel filling, and the illumination of the ultraviolet lamps 66. Upon activation of a switch on the UT Circuit Board, the microprocessor activates the motor 65 for a predetermined but adjustable period of time. The adjustment of this time interval may be presented to the user as a time interval or as an adjustment in the volume of polymerizable solution to be transferred. The motor 65 is then turned off by the microprocessor, and the lamps 66 are energized for a predetermined but user adjustable period of time.

The UI Circuit Board may contain a further switch or switches for controlling the motor 65. A first such switch would allow for replacement of the canister 63 by fully retracting the plunger 64 from the canister. A second switch could allow for manual control of the motor 65, for example to permit priming of the solution injection system after replacement of the canister 63.

As an alternative to the use of a switch on the exterior of the housing, a filling/polymerization cycle can be started automatically upon closure of the drawer unit. For example, a switch may be placed such that it is automatically actuated when the drawer unit is closed. In this case, it is advantageous to place an sensor switch in the filling fixture 30 such that the mechanism can only operate when a gel holder is installed in the fixture.

The apparatus shown in FIG. 6 further shows a reversible belt 67 attached to the drawer unit 22. The belt 67 is supported by a driven and an undriven pulley 68 and 68'. The driven pulley 68 is connected to motor 69, which in turn is connected to a switch 71 on the front of the housing. The motor 69 extends the drawer or retracts the drawer in response to the position of switch 71. The activation of this switch to retract the drawer may also initiate the filling/polymerization cycle.

While the invention has been described with above with reference to the formation of polyacrylamide gels crosslinked using ultra-violet light as an initiator, it will be understood that the invention can also be used with other initiator systems and radiation sources. For example, polymerization of 2–10% (w/v) acrylamide, 19:1 bisacrylamide can be initiated using a radiation source at a wavelength of 450 nm in the presence of 100 $\mu$M methylene blue, 1 mM sodium toluenesulfinate and 50 $\mu$M diphenyliodonium chloride. Similarly, if the cross-linking is achieved with a thermal initiator such as TEMED, IR lamps may be used as the radiation source 66.

After polymerization, the polymerized microgel in the microgel holder is removed from the filling fixture by unscrewing or unclamping the microgel holder. The microgel is now ready to be mounted on a gel running apparatus and loaded with sample to be electrophoresed on the gel.

The apparatus of the present invention is advantageously constructed to utilize a disposable cartridge containing polymerization monomers or prepolymers of the type shown in FIG. 7. The cartridge is formed from a hollow body member 171, having an interior cavity 172 with substantially constant cross-section from a first end A to a point B near an opposing second end, providing a volume of from 5–500 ml, preferably about 50 ml. The interior cavity 172 is tapered at the second end to form a dispensing orifice 173. A slidable plug 174 is sized to tightly slide within the interior cavity 172 in the region of constant cross section and is placed in within a first end of the hollow body member. A cap member 175 for sealing the dispensing orifice 173 is also provided.

Gel forming monomers or prepolymers 176 are disposed within the interior cavity 172, optionally separated from a polymerization initiator 177 by a rupturable seal 178. Preferred gel-forming monomers are acrylamide monomers. Preferred initiators are photopolymerization initiators such as riboflavin or methylene blue.

To fill the cartridges, gel forming materials and polymerization initiators are placed in the interior cavity 172. The plug is then inserted in the wide end of the cartridge. Air is forced out of the cartridge through the dispensing orifice by pressing in on the plug until the gel forming material has displaced all of the air. The dispensing orifice is then capped, for example with a screw-on cap. The wide end may then be covered over with a protective cap (not shown) to insure no movement of the plug during shipment.

When use is required, the cap on the dispensing orifice is removed, and a narrow gauge (i.e., 0.5 to 5 mm diameter) flexible hose (of rubber or silicon or the like) is attached to the narrow end. A luer fitting may be employed to improve the attachment. The opposite end of the hose is connected, preferably with a luer fitting, to the filling bore in the filling fixture manifold. In an alternative format, the hose may be attached to the plug before shipment, and only the distal end of the hose requires connection to the filling bore.

Once the hose is connected, the protective cap of the cartridge is removed, exposing the plug. The prepared cartridge may then be placed in an automated or manual system for the filling of gel cassettes. In a manual system, the prepared cartridge is connected with a snap connection directly to a filling gun such as the DispensGun (TM) (Specialty Products, East Providence, R.I.). The plunger in the gun is adjusted to contact the plug. With each squeeze of the gun's trigger the plunger of the gun drives the plug into the cartridge. The gel forming solution is driven out of the cartridge, through the hose, into the filling fixture bore, and eventually into the cassette.

An automated system uses an automatic dispensing motor which drives the plug into the cartridge at a push of a button. Such automatic dispensing is advantageous in that less variation in solution flow is introduced by human operators.

Cartridges for use with chemically induced polymerization, such as APS/TEMED gels, can also be constructed using a separate barrel-type syringe attached to the side of the main cartridge, or using a cartridge which is divided into two chambers. One chamber is filled with gel forming solution, while the other chamber is filled with a catalyst which hastens polymerization of the gel forming solution. An injection gun with a double pronged plunger is used to inject the correct amount of solutions into a static mixing chamber just above the needle of the cartridge. The mixed solution is driven into the gel cassette by the action of the plungers where it polymerizes.

While the fully automated filling and polymerizing apparatus described above provides for substantial benefits including increased throughput and reliability in the production of electrophoresis gels, in some cases it may be desired to pre-fill the gel holder with unpolymerized material. Thus, as shown in FIG. 8, a further aspect of the invention provides a gel polymerization apparatus comprising a housing 381 and a drawer 361. The drawer 361 is slidably disposed with the housing 381, and is movable between an extended position and a retracted position. The drawer 361 and said housing 381 together form a light tight enclosure when the drawer 361 is in the retracted position. A removable support fixture 30 may be disposed within the drawer 361. The support fixture 30 is adapted to receive a gel holder, and may be substantially identical to the filling fixture described above. Of course, the support fixture need not include means for introducing a polymerizable solution into the gel compartment. Finally, there is a radiation source 66 disposed within the housing in a location effective to irradiate polymerizable solution within the gel compartment of a gel holder in the support fixture. As in the case of the fully automated gel filling and polymerizing apparatus, the lamps may provide ultraviolet, visible or IR radiation depending on the nature of the materials to be polymerized. The apparatus may also include a motor and control devices as in the apparatus shown in FIG. 6.

When a polymerization-only apparatus is used, the gel holder is filled with polymerizable solution outside the apparatus. This can be done manually using a syringe, or manual dispensing gun such as the DispensGun™ available from Specialty Products, East Providence, R.I., or using a motorized plunger of the same type generally employed in the fully automated apparatus. The latter technique is preferred since it reduces variability caused by the operator. Once filled, the gel holders should be promptly transferred to the polymerization apparatus to avoid significant roomlight induced polymerization which may be uneven leading to a less than desirable gel.

The use of a polymerization-only apparatus may be particularly effective on forming gels within microgel holders of the type described in U.S. patent application Ser. No. 08/332,557, and the concurrently filed PCT application which is a continuation in part thereof. Thus, a further aspect of the present invention is a method of preparing an electrophoresis gel comprising the steps of:

(a) filling a gel holder with a gel-forming solution, said gel holder comprising a top substrate, a bottom substrate, and means for sealing the top substrate to the bottom substrate to form a gel compartment having a thickness of 250 microns or less, said means for sealing having an opening therethrough for filling the gel compartment with an unpolymerized gel;

(b) placing the filled gel holder in a polymerization apparatus comprising a housing, a drawer slidably disposed with the housing, said drawer being movable between an extended position and a retracted position, and said drawer and said housing together forming a light tight enclosure when the drawer is in the retracted position, and a radiation source disposed within the housing in a location effective to irradiate polymerizable solution within the gel compartment of a gel holder in the support fixture, said radiation source providing substantially equal amounts of radiation to all parts of the gel holder, said gel holder being placed on the drawer when it is in the extended position;

(c) placing the drawer of the polymerization apparatus in the retracted position, whereby the gel holder is enclosed the light tight enclosure; and (d) irradiating the filled gel holder within the light tight enclosure for a period of time sufficient to polymerize the gel-forming solution. The separation between the two substrates in the gel holder may be defined by a plurality of solid particles, as described in the abovementioned applications, although other means to maintain the spacing may also be used.

EXAMPLE

A UV activated adhesive matrix was prepared using Minico® M07950-R acrylate adhesive from Emerson & Cuming Inc., Woburnm Mass., mixed with 2% by weight Sigma® glass beads (106 micron and finer) filtered to select beads of a size of 45 to 53 microns. The adhesive matrix was screen printed onto the bottom substrate 12 in the pattern shown in FIG. 9. The top substrate 11 was then positioned on top of the bottom substrate 12. The substrates were then exposed to 20 Watts UVA light (wavelength 315–385 nm) to initiate curing of the adhesive and to bond the two substrates together.

After the adhesive was cured, the gel holder was placed horizontally in a filling fixture in accordance with the invention and placed into the top shelf of a device as shown in FIG. 6. A first switch on the UI Circuit Board was manually activated which initiated retraction of the drawer into the housing. Upon full retraction of the drawer, a second switch on the UI Circuit Board was manually activated to commence the filling/polymerization cycle. A polyacrylamide gel forming solution containing 6% acrylamide (19:1 bis-acrylamide), 7 M urea in 0.6×TBE and 10 ppm riboflavin was driven into the gel holder, which was then exposed to ultraviolet light from five 20 W UVA-lamps disposed on the interior of the housing for 10 minutes to polymerize the gel.

We claim:

1. An apparatus for polymerizing a gel, comprising
    (a) a housing;
    (b) an injection system, said injection system connectible to a reservoir for holding a polymerizable solution;
    (c) a filling fixture removably disposed within the housing and adapted to receive a gel holder having an internal gel compartment;
    (d) a solution injection connector adapted to couple the injection system to the internal gel compartment of a gel holder placed within the filling fixture,
    (e) a controller for the injection system, which causes the injection system to inject polymerizable solution from the reservoir directly into the gel compartment without filling the remainder of the housing;
    (f) a radiation source disposed within the housing in a location effective to irradiate polymerizable solution within the gel compartment of a gel holder in the filling fixture, and
    (g) a reservoir connected to the injection system, wherein the reservoir is a cartridge comprising
        a hollow body member having an interior cavity with substantially constant cross-section from a first end to a point near an opposing second end, said cavity being tapered at the second end to form a dispensing orifice;

a slidable plug sized to tightly slide within the interior cavity in the region of constant cross section, said plug being disposed within a first end of the hollow body member;

gel forming monomers or prepolymers disposed within the interior cavity; and a polymerization initiator disposed within the interior cavity.

2. An apparatus according to claim 1, wherein the controller is connected to a switch, and wherein activation of the switch initiates a cycle of filling the gel holder with polymerizable solution and irradiating the gel holder to polymerize the polymerizable solution.

3. An apparatus according to claim 1, wherein the filling fixture is disposed on a drawer slidably disposed within the housing.

4. All apparatus according to claim 3, wherein the drawer has an upper shelf and a lower shelf, and wherein the filling fixture is disposed on the upper shelf and the injection system is disposed on the lower shelf.

5. An apparatus according to claim 4, wherein the reservoir of the injection system is disposed on the lower shelf.

6. An apparatus according to claim 4, further comprising a motor operatively connected to the drawer for retracting and extending the drawer.

7. An apparatus according to claim 6, wherein the controller is connected to a switch, and wherein activation of the switch initiates a cycle of filling the gel holder with polymerizable solution and irradiating the gel holder to polymerize the polymerizable solution, and causes the drawer to be retracted into the housing at the beginning of the cycle and extended from the housing at the end of the cycle.

8. An apparatus according to claim 1, wherein the radiation source irradiates the polymerizable solution with ultraviolet radiation.

9. An apparatus for polymerizing a gel, comprising (a) a housing;

(b) a drawer slidably disposed with the housing, said drawer being movable between an extended position and a retracted position, and said drawer and said housing together forming a light tight enclosure when the drawer is in the retracted position;

(c) a support fixture removably disposed within the drawer and adapted to receive a gel holder having an internal gel compartment containing a polymerizable solution; and (d) a radiation source disposed within the housing in a location effective to irradiate polymerizable solution within the gel compartment of a gel holder in the support fixture, said radiation source providing substantially equal amounts of radiation to all parts of the gel holder.

10. An apparatus according to claim 9, wherein the radiation source comprises a plurality of individual lamps.

11. An apparatus according to claim 10, wherein the lamps are ultra-violet lamps.

12. An apparatus according to claim 10, wherein the lamps provide radiation at a wavelength of 450 nm.

13. A method of preparing an electrophoresis gel comprising the steps of:

(a) filling a gel holder with a gel-forming solution, said gel holder comprising a top substrate, a bottom substrate, and means for scaling the top substrate to the bottom substrate to form a gel compartment having a thickness of 250 microns or less, said means for scaling having an opening therethrough for filling the gel compartment with an unpolymerized gel;

(b) placing the filled gel holder in a polymerization apparatus comprising a housing, a drawer slidably disposed with the housing, said drawer being movable between an extended position and a retracted position, and said drawer and said housing together forming a light tight enclosure when the drawer is in the retracted position, and a radiation source disposed within the housing in a location effective to irradiate polymerizable solution within the gel compartment of a gel holder in the support fixture, said radiation source providing substantially equal amounts of radiation to all parts of the gel holder, said gel holder being placed on the drawer when it is in the extended position;

(c) placing the drawer of the polymerization apparatus in the retracted position, whereby the gel holder is enclosed the light tight enclosure; and (d) irradiating the filled gel holder within the light tight enclosure for a period of time sufficient to polymerize the gel-forming solution.

14. The method according to claim 13, wherein the gel-forming solution comprises acrylamide monomers and a photoinitiator.

15. The method according to claim 14, wherein the photoinitiator is methylene blue.

16. The method according to claim 14, wherein the photoinitiator is riboflavin.

17. A method according to claim 13, wherein the means for sealing the substrates comprises an adhesive applied between the top and bottom substrates along at least two opposing edges of the top and bottom substrates.

18. The method according to claim 17, wherein the gel holder further comprises a plurality of solid particles, said solid particles being disposed between the top and bottom substrate and having a mean diameter substantially equal to the thickness of the gel compartment, and at least a portion of the particles are disposed within the adhesive.

19. The method according to claim 13, wherein the gel holder further comprises a plurality of solid particles, said solid particles being disposed between the top and bottom substrate and having a mean diameter substantially equal to the thickness of the gel compartment.

20. The method according to claim 19, wherein at least a portion of the solid particle are affixed to the top or bottom substrate by the steps of forming a mixture of a powder of a low melting glass with a plurality of the solid particles; dispersing the mixture on a surface of the substrate; heating the substrate and mixture to melt the low melting glass powder; and cooling the heated substrate to resolidify the low melting glass, whereby a bond between the solid particles and the substrate is formed.

* * * * *